United States Patent
Sauli

[11] 3,948,935
[45] Apr. 6, 1976

[54] PYRAZOLINE DERIVATIVES

[75] Inventor: Michel Sauli, Paris, France

[73] Assignee: Rhone-Poulenc S.A., Paris, France

[22] Filed: July 15, 1974

[21] Appl. No.: 488,678

[30] Foreign Application Priority Data
July 17, 1973   France .............................. 73.26153
May 8, 1974     France .............................. 74.15939

[52] U.S. Cl............ 260/310 D; 260/310 A; 424/200
[51] Int. Cl.².......................................... C07D 231/08
[58] Field of Search...... 260/310 R, 310 D; 424/200

[56] References Cited
UNITED STATES PATENTS
| | | | |
|---|---|---|---|
| 2,754,244 | 7/1956 | Gysin et al. ................ | 260/310 R |
| 3,825,557 | 7/1974 | Hoffman et al. ............ | 260/310 R |
| 3,847,936 | 11/1974 | Adolphi et al. .............. | 260/310 A |

FOREIGN PATENTS OR APPLICATIONS
| | | | |
|---|---|---|---|
| 300,742 | 8/1954 | Switzerland................. | 260/310 R |

*Primary Examiner*—Donald B. Meyer
*Attorney, Agent, or Firm*—Stevens, Davis, Miller & Mosher

[57] ABSTRACT

Pyrazoline compounds of the formula:-

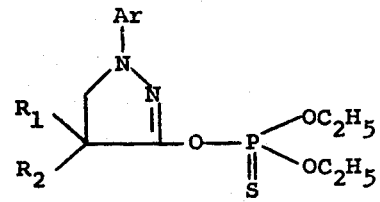

wherein Ar represents phenyl optionally substituted by at most three atoms or radicals selected from halogen, alkyl and alkoxy of 1 through 4 carbon atoms, trifluoromethyl and nitro, and $R_1$ and $R_2$ represent hydrogen or methyl, are new compounds possessing insecticidal, acaricidal and nematicidal properties.

14 Claims, No Drawings

PYRAZOLINE DERIVATIVES

This invention relates to new derivatives of pyrazoline, to a process for their preparation, and compositions containing them.

BACKGROUND OF THE INVENTION

A wide variety of organic phosphate and thiophosphate esters are known to be useful as insecticides and acaricides. In such compounds, the phosphate or thiophosphate residue may be attached to a heterocyclic nucleus. For example, the United States Patent No. 2,754,244, granted July 10th 1956 to Hans Gysin et al, discloses pyrazolyl phosphoric and thiophosphoric acid esters which are stated to have good insecticidal and acaricidal activity. However, it has been found that the utility of such esters varies widely with the nature of the organic radicals that they contain, and that even small changes in chemical structure can give rise to substantial differences in insecticidal and acaricidal activity. Substantial research has therefore been directed towards finding compounds of this general type having the most desirable combination of properties, particularly high and wide-ranging insecticidal and acaricidal activity combined with relatively low toxicity to warm-blooded animals and a persistence suited to the end use envisaged. The present invention provides new thiophosphoric acid esters in which the thiophosphoric ester residue is attached to a pyrazoline nucleus.

The pyrazoline derivatives of the present invention are the $\Delta^2$-pyrazoline compounds of the general formula:-

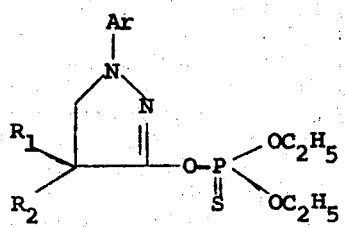
I wherein Ar represents a phenyl radical optionally substituted by one, two or three atoms or radicals, which may be the same or different, selected from halogen (preferably chlorine) atoms, alkyl and alkoxy radicals each containing 1 to 4 carbon atoms, the trifluoromethyl radical and the nitro radical, and $R_1$ and $R_2$ are the same or different and each represents a hydrogen atom or the methyl radical.

According to a feature of the invention, these pyrazoline derivatives are prepared by the process which comprises reacting 0,0-diethylchlorothiophosphate with a pyrazolidinone of the general formula:

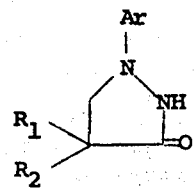
II which, in an alkaline medium, reacts in the tautomeric enol form:

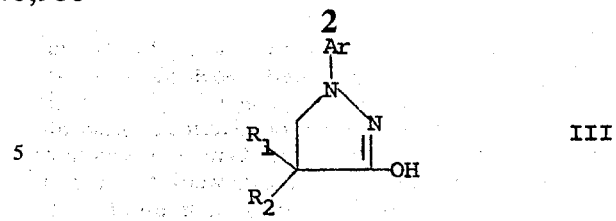
III the symbols Ar, $R_1$ and $R_2$ being as hereinbefore defined. An alkali metal derivative of a compound of general formula III, optionally prepared in situ, is generally used.

The reaction is preferably carried out in an organic solvent such as 2-N-methylpyrrolidone, dimethylformamide, hexamethylphosphotriamide or dimethylsulphoxide, at a temperature between 0° and 30°C.

The pyrazolidinone derivatives of general formula II can be prepared by reacting a β-halogenated acid halide of the general formula:

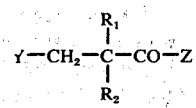

$$Y-CH_2-\underset{\underset{R_2}{|}}{\overset{\overset{R_1}{|}}{C}}-CO-Z \qquad IV$$

wherein Y represents a halogen atom, e.g. chlorine, bromine or iodine, and Z represents a halogen (preferably chlorine) atom, with a hydrazine of the general formula:

$$Ar - NH - NH_2 \qquad V$$

wherein Ar is as hereinbefore defined.

The pyrazoline derivatives of general formula I possess useful insecticidal and acaricidal properties. They are particularly active through contact and by direct ingestion, especially against diptera, coleoptera, lepidoptera, hemiptera and orthoptera. They are also excellent soil insecticides.

The pyrazoline derivatives also possess useful nematicidal activity. They have proved particularly active in vivo against *Ditylenchus dipsaci* and *Meloidogyne incognita* at rates of application of between 1 and 100 kg. per hectare and are preferably used in the treatment of soil in the form of dusts.

According to a further feature of the present invention, there are provided insecticidal, acaricidal and nematicidal compositions containing, as the active ingredient, at least one pyrazoline derivative of formula I in association with one or more diluents or adjuvants compatible with the pyrazoline derivative(s) and suitable for use in agricultural insecticidal, acaricidal and nematicidal compositions. Preferably the compositions contain between 0.005 and 80% by weight of pyrazoline derivative.

The compositions may be solid if there is employed a powdered solid compatible diluent such as talc, calcined magnesia, kieselguhr, tricalcium phosphate, powdered cork, adsorbent charcoal, or a clay such as kaolin or bentonite. These solid compositions are preferably prepared by grinding the pyrazoline derivative with the solid diluent, or by impregnating the solid diluent with a solution of the pyrazoline derivative in a volatile solvent, evaporating the solvent, and if necessary grinding the product so as to obtain a powder.

Instead of a solid diluent, there may be used a liquid in which the pyrazoline derivative is dissolved or dispersed. The compositions may thus take the form of suspensions, emulsions or solutions in organic or aqueous-organic media, for example acetophenone, aromatic hydrocarbons such as toluene or xylene or mineral, animal or vegetable oils, or mixtures of these diluents. The compositions in the form of suspensions, emulsions or solutions may contain wetting, dispersing or emulsifying agents of the ionic or non-ionic type, for example sulphoricinoleates, quaternary ammonium derivatives or products based on condensates of ethylene oxide, such as the condensates of ethylene oxide with octylphenol, or fatty acid esters of anhydrosorbitols which have been rendered soluble by etherification of the free hydroxyl groups by condensation with ethylene oxide. It is preferable to use agents of the non-ionic type because they are not sensitive to electrolytes. When emulsions are required, the pyrazoline derivatives may be used in the form of self-emulsifying concentrates containing the active substance dissolved in the emulsifying agent or in a solvent containing an emulsifying agent compatible with the pyrazoline derivative and solvent, a simple addition of water to such concentrates producing compositions ready for use.

The pyrazoline derivatives of general formula I are preferably employed in a quantity of 10 to 100 g. per hectoliter of water when they are used for spraying at a rate of approximately 1 hectoliter per hectare.

In the treatment of soil, the best results are obtained by using the pyrazoline derivatives at a rate of 1 to 100 kg. of active material per hectare.

The pyrazoline derivatives of general formula I wherein Ar represents a phenyl radical substituted by one, two or three atoms or radicals selected from chlorine and the nitro radical, the phenyl radical carrying at most one nitro radical, and $R_1$ and $R_2$ are the same or different and each represents a hydrogen atom or the methyl radical, are of outstanding interest.

The following compounds are especially active as insecticides and acaricides:

1-(2,4-dichlorophenyl)-3-0,0-diethylthionophosphoryl-$\Delta^2$-pyrazoline, 1-(4-chlorophenyl)-3-0,0-diethylthionophosphoryl-$\Delta^2$-pyrazoline, 1-(2,4,5-trichlorophenyl)-3-0,0-diethylthionophosphoryl-$\Delta^2$-pyrazoline, 1-(3,5-dichlorophenyl)-3-0,0-diethylthionophosphoryl-$\Delta^2$-pyrazoline, 1-(3-chlorophenyl)-3-0,0-diethylthionophosphoryl-$\Delta^2$-pyrazoline, 1-(4-nitrophenyl)-3-0,0-diethylthionophosphoryl-$\Delta^2$-pyrazoline and 1-(2-chloro-4-nitrophenyl)-3-0,0-diethylthionophosphoryl-$\Delta^2$-pyrazoline.

The following compounds are especially active as nematicides:

1-(3,5-dichlorophenyl)-3-0,0-diethylthionophosphoryl-$\Delta^2$-pyrazoline, 1-(3-chlorophenyl)-3-0,0-diethylthionophosphoryl-$\Delta^2$-pyrazoline, 1-(2-chlorophenyl)-3-0,0-diethylthionophosphoryl-4,4-dimethyl-$\Delta^2$-pyrazoline, 1-(4-nitrophenyl)-3-0,0-diethylthionophosphoryl-$\Delta^2$-pyrazoline and 1-(2-chloro-4-nitrophenyl)-3-0,0-diethylthionophosphoryl-$\Delta^2$-pyrazoline.

The following Examples illustrate the preparation of pyrazoline derivatives of the present invention.

EXAMPLE 1

A 22.5% (w/v) solution of potassium ethoxide in ethanol (21.2 cc.) is added to a solution of 1-(2,4-dichlorophenyl)pyrazolidin-3-one (12.8 g.) in N-methylpyrrolidone (120 cc.). The solution obtained is kept at between 5° and 10°C and 0,0-diethylchlorothiophosphate (10.3 g.) is added dropwise over the course of 5 minutes. The mixture is stirred for approximately 15 hours at a temperature of about 20°C. The reaction mixture is then poured into ice-water (600 cc.) and the oil which separates is extracted with cyclohexane (successively 150 cc. and then 2 × 100 cc.). The combined organic layers are washed successively with distilled water (300 cc.), a 10% (w/v) aqueous solution of potassium bicarbonate (250 cc.), and distilled water (300 cc.). After drying over anhydrous sodium sulphate and concentration under reduced pressure, 1-(2,4-dichlorophenyl)-3-0,0-diethylthionophosphoryl-$\Delta^2$-pyrazoline (14.2 g.) is obtained in the form of an oil with a refractive index $n_D^{20} = 1.5775$.

1-(2,4-Dichlorophenyl)pyrazolidin-3-one (m.p. 202°C), used as starting material, can be prepared by reacting $\beta$-bromopropionic acid chloride with 2,4-dichlorophenylhydrazine.

EXAMPLES 2 to 11

Following the procedure of Example 1 and employing appropriate pyrazolidinone starting materials of general formula II, there are obtained the following products:-

2. 1-(2,4-dichlorophenyl)-3-0,0-diethylthionophosphoryl-4,4-dimethyl-$\Delta^2$-pyrazoline, an oil: $n_D^{20} = 1.5430$;
3. 1-(4-chlorophenyl)-3-0,0-diethylthionophosphoryl-4,4-dimethyl-$\Delta^2$-pyrazoline, an oil: $n_D^{20} = 1.5470$;
4. 1-(4-chlorophenyl)-3-0,0-diethylthionophosphoryl-$\Delta^2$-pyrazoline, m.p. 70°C.;
5. 1-(2,4,5-trichlorophenyl)-3-0,0-diethylthionophosphoryl-$\Delta^2$-pyrazoline, an oil: $n_D^{20} = 1.5852$;
6. 1-phenyl-3-0,0-diethylthionophosphoryl-4,4-dimethyl-$\Delta^2$-pyrazoline, an oil: $n_D^{20} = 1.545-1.550$;
7. 1-(2-chlorophenyl)-3-0,0-diethylthionophosphoryl-$\Delta^2$-pyrazoline, an oil: $n_D^{20} = 1.5565$;
8. 1-(3,5-dichlorophenyl)-3-0,0-diethylthionophosphoryl-$\Delta^2$-pyrazoline, an oil: $n_D^{20} = 1.5898$;
9. 1-(3-chlorophenyl)-3-0,0-diethylthionophosphoryl-$\Delta^2$-pyrazoline, an oil: $n_D^{20} = 1.5780$; 10. 1-(2-chlorophenyl)-3-0,0-diethylthionophosphoryl-4,4-dimethyl-$\Delta^2$-pyrazoline, an oil: $n_D^{20} = 1.5355$, and
11. 1-(3-chlorophenyl)-3-0,0-diethylthionophosphoryl-4,4-dimethyl-$\Delta^2$-pyrazoline, an oil: $n_D^{20} = 1.5493$

EXAMPLE 12

A 22.5% (w/v) solution of potassium ethoxide in ethanol (36.4 cc.) is added to a solution of 1-(4-nitrophenyl)pyrazolidin-3-one (20.7 g.) in N-methylpyrrolidone (180 cc.). The solution obtained is kept at between 5° and 10°C and 0,0-diethylchlorothiophosphate (18.8 g.) is added dropwise over the course of 10 minutes. The mixture is stirred for approximately 15 hours at a temperature of about 20°C. This reaction mixture is then poured into icewater (500 cc.). The precipitate which forms is filtered off and then taken up in methylene chloride (200 cc.). The solution obtained is washed successively with distilled water (100 cc.), a 4% (w/v) aqueous solution of sodium hydroxide (100 cc.) and distilled water (2 × 100 cc.). After drying over anhydrous sodium sulphate and concentration under reduced pressure, a solid (38 g.) is obtained which is recrystallised from ethanol. 1-(4-Nitrophenyl)-3-0,0-diethylthionophosphoryl-$\Delta^2$-pyrazoline (19 g.), melting at 107°C, is thus obtained.

1-(4-Nitrophenyl)pyrazolidin-3-one (m.p. 227°C), used as starting material, can be prepared by reacting β-bromopropionic acid chloride with 4-nitrophenylhydrazine.

EXAMPLE 13

A 22.5% (w/v) solution of potassium ethoxide in ethanol (13.2 cc.) is added to a solution of 1-(2-chloro-4-nitrophenyl)pyrazolidin-3-one (12.1 g.) in N-methylpyrrolidone (90 cc.). The solution is kept at between 5° and 10°C and O,O-diethylchlorothiophosphate (9.4 g.) is added dropwise over the course of 10 minutes. The reaction mixture is stirred for approximately 15 hours at a temperature of about 20°C. The reaction mixture is then poured into ice-water (500 cc.) and the oil which separates is extracted with methylene chloride (150 cc.). The organic layer obtained is washed successively with distilled water (150 cc.), a 4% (w/v) aqueous solution of sodium hydroxide (100 cc.), and distilled water (2 × 250 cc.). After drying over anhydrous sodium sulphate and concentration under reduced pressure, the residue obtained is recrystallised from ethanol. 1-(2-Chloro-4-nitrophenyl)-3-O,O-diethylthionophosphoryl-$\Delta^2$-pyrazoline (14.3 g.), melting at 79° C, is thus obtained.

1-(2-Chloro-4-nitrophenyl)pyrazolidin-3-one (m.p. 205°C), used as starting material, can be prepared by reacting β-bromopropionic acid chloride with 2-chloro-4-nitrophenylhydrazine.

The following Examples illustrate compositions of the invention, said compositions including a pyrazoline derivative of general formula I.

EXAMPLE 14

A condensation product of octylphenol and ethylene oxide containing 10 moles of ethylene oxide per mole of octylphenol (10 parts by weight) is added to a solution of 1-(2,4-dichlorophenyl)-3-O,O-diethylthionophosphoryl-$\Delta^2$-pyrazoline (25 parts by weight) in a mixture of equal parts (by volume) of toluene and acetophenone (65 parts by volume). The resulting solution is used, after dilution with water in the ratio of 200 cc. of this solution per 100 liters of water, as an insecticidal, acaricidal or nematicidal composition in agricultural situations.

EXAMPLE 15

A condensation product of octylphenol and ethylene oxide containing 10 moles of ethylene oxide per mole of octylphenol (10 parts by weight) is added to a solution of 1-(4-nitrophenyl)-3-O,O-diethylthionophosphoryl-$\Delta^2$-pyrazoline (25 parts by weight) in a mixture of equal parts (by volume) of toluene and acetophenone (65 parts by volume). The resulting solution is used, after dilution with water, in the ratio of 200 cc. of this solution per 100 liters of water, as an insecticidal, acaricidal or nematicidal composition in agricultural situations.

The insecticidal, acaricidal and nematicidal activities of the pyrazoline derivatives of the present invention is demonstrated by the following tests:

1. Insecticidal activity by contact (fly, beetle)

A solution (1cc.), in acetone, of the product to be investigated at a given concentration is sprayed into a 120 cc. glass jar leaving a film of the product inside the jar. When the solvent has evaporated, the insects (5 flies or 10 beetles) are placed in the jars which are then covered with a metal gauze. The number of insects which have died after 24 hours of contact in the case of the flies and after 3 days of contact in the case of the beetles is counted. The concentration of pyrazoline derivative in grams per cc. which causes the death of 90% of the insects is determined.

| Product of Example | Fly | Beetle |
|---|---|---|
| 1 | $10^{-6}$ | $3 \times 10^{-6}$ |
| 2 | $5 \times 10^{-6}$ | $10^{-4}$ |
| 3 | $10^{-5}$ | $10^{-5}$ |
| 4 | $5 \times 10^{-6}$ | $10^{-5}$ |
| 5 | $10^{-6}$ | $3 \times 10^{-6}$ |
| 6 | $5 \times 10^{-4}$ | $10^{-3}$ |
| 7 | $2 \times 10^{-5}$ | $10^{-5}$ |
| 8 | $10^{-5}$ | $5 \times 10^{-6}$ |
| 9 | $2 \times 10^{-5}$ | $10^{-5}$ |
| 10 | $5 \times 10^{-5}$ | $5 \times 10^{-5}$ |
| 11 | $10^{-5}$ | $10^{-5}$ |
| 12 | $10^{-5}$ | $3 \times 10^{-5}$ |
| 13 | $3 \times 10^{-6}$ | $10^{-5}$ |

2. Insecticidal activity by contact (topical treatment of insects; fly, cricket)

A known amount of an aqueous-acetone solution of the product to be investigated is deposited, using a micro-syringe of the "Agla" or "Hamilton" type, on the prothorax of each insect, at an amount of 0.001 cc. per fly or 0.003 cc. per cricket. The insects are anaesthetised by means of carbon dioxide. The test is carried out using different concentrations of the pyrazoline derivatives. The mortality rate is determined 24 hours after treatment in the case of the flies and 3 days after the treatment in the case of the crickets. The concentration of active product which causes 50% mortality is determined.

| Product of Example | Fly | Cricket |
|---|---|---|
| 1 | $6 \times 10^{-5}$ | $10^{-3}$ |
| 2 | $3 \times 10^{-4}$ | $>10^{-2}$ |
| 3 | $>10^{-3}$ | $>10^{-2}$ |
| 4 | $8 \times 10^{-5}$ | $10^{-3}$ |
| 5 | $6 \times 10^{-5}$ | $10^{-3}$ |
| 7 | $3 \times 10^{-4}$ | $10^{-3}$ |
| 12 | $10^{-4}$ | $3 \times 10^{-4}$ |
| 13 | $10^{-4}$ | $3 \times 10^{-4}$ |

3. Insecticidal activity by contact-ingestion (foliage treated by immersion; *Plutella maculipennis* caterpillars, *Prodenia litura* caterpillars and *Pieris brassicae* caterpillars)

Young cabbage leaves are immersed for 10 seconds in the solutions to be investigated. When they are dry, they are infested with the following parasites: *Plutella maculipennis*, *Prodenia litura* or *Pieris brassicae* caterpillars (larvae 3rd stage). The number of deaths are counted 3 days after the treatment. The concentration of pyrazoline derivative which causes the deaths of 90% of the caterpillars is determined.

| Product of Example | Plutella | Prodenia | Pieris |
|---|---|---|---|
| 1 | $5 \times 10^{-5}$ | $2 \times 10^{-4}$ | $2 \times 10^{-4}$ |
| 2 | $3 \times 10^{-4}$ | $3 \times 10^{-3}$ | |
| 3 | $10^{-4}$ | $3 \times 10^{-3}$ | $5 \times 10^{-4}$ |
| 4 | $5 \times 10^{-5}$ | $5 \times 10^{-4}$ | $2 \times 10^{-4}$ |
| 5 | | $10^{-4}$ | $10^{-4}$ |
| 7 | $3 \times 10^{-4}$ | $10^{-3}$ | $10^{-4}$ |
| 8 | $2 \times 10^{-4}$ | $3 \times 10^{-4}$ | $10^{-4}$ |
| 9 | $10^{-3}$ | $10^{-3}$ | $3 \times 10^{-4}$ |
| 10 | $3 \times 10^{-4}$ | | $10^{-3}$ |
| 12 | $10^{-4}$ | $3 \times 10^{-4}$ | $10^{-4}$ |

| Product of Example | Plutella | Prodenia | Pieris |
|---|---|---|---|
| 13 | $10^{-4}$ | $3 \times 10^{-4}$ | $3 \times 10^{-5}$ |

4. Acaricidal activity by contact-ingestion (foliage treated by immersion; *Tetranychus telarius*, parthenogenetic females)

Leaves of bean plants at the cotyledonary leaf stage are immersed for 10 seconds in the solution of the product to be investigated. After drying, the leaves are infested with parasites from highly contaminated leaves of bean plants. The contaminated bean plants are kept alive by immersing the roots and the base of the stem in distilled water. The number of deaths are counted 2 to 4 days after contamination. The concentration of pyrazoline derivatives which causes the death of 90% of the mites is determined.

| Procuct of Example | Tetranychus telarius |
|---|---|
| 1 | $3 \times 10^{-5}$ |
| 2 | $3 \times 10^{-5}$ |
| 3 | $5 \times 10^{-5}$ |
| 4 | $10^{-4}$ |
| 5 | $10^{-4}$ |
| 6 | $10^{-3}$ |
| 7 | $10^{-3}$ |
| 8 | $10^{-4}$ |
| 9 | $10^{-4}$ |
| 10 | $2 \times 10^{-4}$ |
| 11 | $10^{-4}$ |
| 12 | $10^{-3}$ |
| 13 | $10^{-3}$ |

5. Nematicidal activity (soil treatment; *Meloidogyne incognita*)

The soil is contaminated with *Meloidogyne incognita* in such a way that there are 10,000 eggs per liter of soil. A mixture of the product to be investigated with Atta-clay is incorporated into the soil. After 2 weeks, 1 month old tomato plants are planted out. The number of galls formed on the roots is counted 3 weeks after the planting out. The concentration of pyrazoline derivative, expressed in kg. per hectare, which provides the plants with 95 to 100% protection (AC $_{95-100}$), is determined.

| Product of Example | Meloidogyne incognita |
|---|---|
| 12 | 40 |
| 13 | 20 |

6. Nematicidal activity (soil treatment; *Ditylenchus dipsaci*)

Clover seeds are sown in a soil into which a suspension of the product to be investigated has been incorporated beforehand. The soil is sprinkled with the inoculum solution (obtained from contaminated clover plants). The number of plantlets attacked by nematodes is counted 12 to 15 days after sowing. The concentration of pyrazoline derivative, expressed in kg. per hectare, which provides 95 to 100% of the plantlets with protection (AC $_{95-100}$), is determined.

| Product of Example | Ditylenchus dipsaci |
|---|---|
| 8 | 50 |
| 9 | 25 |
| 10 | 100 |
| 12 | 10 – 20 |
| 13 | 1 – 5 |

It is to be noted that in this specification 0,0-diethyl-chlorothiophosphate is the compound of the structure $Cl.PS(OC_2H_5)_2$, and the radical termed "0,0-diethylthionophosphoryl" has the structure $-O.PS(OC_2H_5)_2$.

I claim:

1. A pyrazoline of the formula:

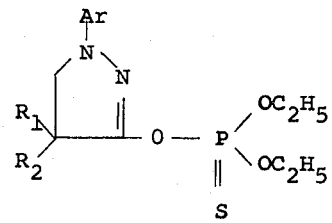

wherein Ar represents phenyl, or phenyl substituted by up to three substituents selected from the class consisting of chlorine and nitro, the phenyl radical carrying at most one nitro radical, and $R_1$ and $R_2$ each represent hydrogen or methyl.

2. The pyrazoline according to claim 1 which is 1-(2,4-dichlorophenyl)-3-0,0-diethylthionophosphoryl-$\Delta^2$-pyrazoline.

3. The pyrazoline according to claim 1 which is 1-(4-chlorophenyl)-3-0,0-diethylthionophosphoryl-$\Delta^2$-pyrazoline.

4. The pyrazoline according to claim 1 which is 1-(2,4,5-trichlorophenyl)-3-0,0-diethylthionophosphoryl-$\Delta^2$-pyrazoline.

5. The pyrazoline according to claim 1 which is 1-(3,5-dichlorophenyl)-3-0,0-diethylthionophosphoryl-$\Delta^2$-pyrazoline.

6. The pyrazoline according to claim 1 which is 1-(3-chlorophenyl)-3-0,0-diethylthionophosphoryl-$\Delta^2$-pyrazoline.

7. The pyrazoline according to claim 1 which is 1-(4-nitrophenyl)-3-0,0-diethylthionophosphoryl-$\Delta^2$-pyrazoline.

8. The pyrazoline according to claim 1 which is 1-(2-chloro-4-nitrophenyl)-3-0,0-diethylthionophosphoryl-$\Delta^2$-pyrazoline.

9. The pyrazoline according to claim 1 which is 1-(2-chlorophenyl)-3-0,0-diethylthionophosphoryl-4,4-dimethyl-$\Delta^2$-pyrazoline.

10. The pyrazoline according to claim 1 which is 1-(2,4-dichlorophenyl)-3-0,0-diethylthionophosphoryl-4,4-dimethyl-$\Delta^2$-pyrazoline.

11. The pyrazoline according to claim 1 which is 1-(4-chlorophenyl)-3-0,0-diethylthionophosphoryl-4,4-dimethyl-$\Delta^2$-pyrazoline.

12. The pyrazoline according to claim 1 which is 1-phenyl-3-0,0-diethylthionophosphoryl-4,4-dimethyl-$\Delta^2$-pyrazoline.

13. The pyrazoline according to claim 1 which is 1-(2-chlorophenyl)-3-0,0-diethylthionophosphoryl-$\Delta^2$-pyrazoline.

14. The pyrazoline according to claim 1 which is 1-(3-chlorophenyl)-3-0,0-diethylthionophosphoryl-4,4-dimethyl$\Delta^2$-pyrazoline.

* * * * *